United States Patent [19]

Sipos et al.

[11] 4,364,927

[45] Dec. 21, 1982

[54] SULFONATED NAPHTHALENE FORMALDEHYDE CONDENSATION POLYMERS AS DENTAL PLAQUE BARRIERS

[75] Inventors: Tibor Sipos, Lebanon; Henry F. Motkowski, Jr., Hamilton Square, both of N.J.

[73] Assignee: Johnson & Johnson Products, Inc., New Brunswick, N.J.

[21] Appl. No.: 172,351

[22] Filed: Jul. 25, 1980

[51] Int. Cl.$^3$ ............... A61K 7/16; A61K 31/185; A61K 31/765; A61K 31/775
[52] U.S. Cl. ............................. 424/56; 424/54; 424/82; 424/289; 424/315; 424/316
[58] Field of Search ............... 424/48–56, 424/78, 82, 289, 315, 316; 260/505 R, 512; 528/230

[56] References Cited

U.S. PATENT DOCUMENTS 3,320,212 5/1967 Shen et al. ............... 424/56
3,919,429 11/1975 Grossmann et al. ............... 424/78

FOREIGN PATENT DOCUMENTS 1960812 4/1969 Fed. Rep. of Germany ...... 260/512
2444785 4/1976 Fed. Rep. of Germany ...... 424/315
1507772 4/1978 United Kingdom .

*Primary Examiner*—Douglas W. Robinson

[57] ABSTRACT

Compositions and methods for preventing the attachment of dental plaque to the surfaces of the teeth of mammals comprise condensation polymers of formaldehyde with naphthalene sulfonic acid as well as the pharmaceutically acceptable salts thereof in a pharmaceutically acceptable vehicle, and the periodic application thereof of teeth.

8 Claims, No Drawings

SULFONATED NAPHTHALENE FORMALDEHYDE CONDENSATION POLYMERS AS DENTAL PLAQUE BARRIERS

TECHNICAL FIELD

This invention relates to oral hygiene compositions and methods using such compositions to prevent attachment of bacteria to teeth. More particularly, it relates to certain sulfonated polymeric materials that have been found useful in inhibiting the agglutination of oral microbes on teeth.

BACKGROUND ART

The prevention of the deposition of dental plaque on teeth is a highly desired result. Dental plaque results when cariogenic bacteria aggregate in colonies on the surface of teeth and form a tenacious deposit thereon. The presence of plaque on teeth is believed to be a precursor to development of gingivitis, dental caries and periodontal disease.

While many attempts have been made to control the effects of cariogenic bacteria and the dental plaque they produce, for example, fluoride, flossing, brushing, etc., treatments, these are typically directed to either counteracting the secondary effects of plaque on the teeth and gums, or to the removal of plaque that is already formed on and adhering to the teeth and surrounding tissue. Such treatments are not, however, entirely successful, and must be supplemented with periodic treatment by dental professionals. To date, there is no commercially feasible home treatment method for preventing the formation of plaque or its adhesion to teeth.

Condensation polymers of formaldehyde with naphthalene sulfonic acid are well known in commerce. They generally are of relatively low molecular weight, of the order of between about 500 and 5,000, typically about 2,000. Their sodium salts are commonly used as dispersants for pigments and other particles in aqueous media. Typical applications include latex paints, agricultural chemical formulations, pesticides and paper coatings. These materials are available commercially under the TAMOL trademark from Rohm & Haas Company and under the LOMAR trademark from the Process Chemical Division of Diamond Shamrock Chemical Company. To our knowledge, they have not been used in any compositions for treatment of the oral cavity or teeth.

THE INVENTION

We have discovered that certain alkali metal as well as multivalent metal salts of these condensation polymers inhibit the deposition of dental plaque onto human teeth. These hydrophilic polymeric sulfonates have good film forming characteristics and, accordingly, are applied to teeth from various dentifrice formulations, mouth rinses, or other oral hygiene procedures. The anionic sulfonate polmers are substantially soluble in water or water/organic solvent vehicles, primarily because of the relatively high degree of sulfonation achieved during preparation of these derivatives. While the mechanism of action of the hydrophilic polymeric films in retarding plaque deposition is not known with absolute certainty, it is presumed that the films of anionically-charged polymers deposited on teeth effect a mutual repulsion between the negatively charged polymer film and the negatively charged microorganisms in oral fluids responsible for plaque generation. For example, when powdered human dental enamel is dispersed in the aqueous media containing salts of the polymeric sulfonates, a substantially negative surface charge is imparted to the enamel particles, as determined by zeta potential measurements. The sulfonated polymers of this invention are especially effective as components of dentifrices and other oral hygiene preparations in reducing dental plaque deposition on teeth.

The hydrophilic, polymeric sulfonates found useful for dental plaque control in accordance with the present invention are essentially formaldehyde condensation polymers of naphthalene sulfonic acids, typically the 2-monosulfonic acid. Generally,, these are employed in the form of a pharmaceutically acceptable salt wherein the cation is selected from the group consisting of lithium, sodium, potassium, calcium, magnesium, zinc, aluminum, hydrogen, ammonium and substituted ammonium ions derived from pharmaceutically acceptable organic amines. In general, the metal and ammonium salts are preferred over the free sulfonic acid derivatives because of their higher water solubility and lower degree of acidity (closer to neutrality), thereby favoring their use in oral hygiene formulations for dental plaque control. The sodium and zinc salts are particularly preferred.

As indicated in general structure (I), the exact position or orientation of the methylene (—$CH_2$—) linkages on the aromatic rings is not known and is generally recognized as being complex and varied. It is understood that some of the formaldehyde linkages may not be solely of the —$CH_2$— type but can also involve some extended units, such as $CH_2OCH_2$ and $CH_2(OCH_2)_nOCH_2$, or other possibilities, although the formaldehyde linkages are believed to consist essentially of the methylene linkage depicted in structure I. Similarly, while the naphthalene ring is believed to be monosulfonated primarily in the 2-position as shown, there may be some of the 1-isomer as well.

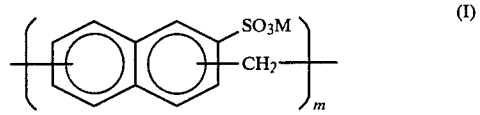

(I)

The sulfonated formaldehyde polymers of this invention are substantially soluble in water or mixed solvents comprising water and an organic solvent miscible therewith (generally at least 1% w/w). The degree of sulfonation (D.S.), defined herein as the average number of sulfonate or sulfonic acid groups per repeat unit of the polymeric structure, is an important variable which has a significant effect on the extent of dental plaque deposition.

As implied above and in structure (I), the commercially available sulfonated polymers used in this invention are understood to be prepared by condensation of formaldehyde with naphthalene sulfonic acid and therefore have a degree of sulfonation of essentially 1. However, the present invention is not restricted to the use of these commercially available polymers, but includes analogous formaldehyde/naphthalene condensation products wherein the degree of sulfonation is in the range of from about 0.4 to about 1.4. These can be depicted as having structure (II),

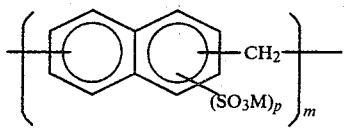

(II)

wherein M is a cation as defined above and the subscript p has a value of from about 0.4 to about 1.4.

The polymers of this invention having a D.S. substantially different from 1 are generally prepared by aromatic sulfonation of naphthalene formaldehyde condensation polymer precursors.

The naphthalene formaldehyde polymer precursors are prepared by heating approximately equimolar quantities of formaldehyde and naphthalene in an inert solvent, in the presence of an acid catalyst such as sulfuric acid, p-toluenesulfonic acid, methanesulfonic acid, or perchloric acid, for several hours. The preferred solvent for the reaction is acetic acid.

Preferred sulfonation agents are anhydrous sulfur trioxide, triethyl phosphate (TEP) complexes of sulfur trioxide, and chlorosulfonic acid. Sulfonations are effected in solvents such as methylene chloride, 1,2-dichloroethane, and chloroform. Temperature control of the sulfonation reaction is not very critical. Acceptable results are obtained over a temperature range of $-20°$ C. to $+40°$ C. range. Sulfonations are generally effected at ambient room temperatures, since the sulfonation exotherm is very mild and rarely results in temperature increases beyond 35° C.

Typical impurities in the sulfonated polymer are small amounts of unreacted polymer and excess sulfonation agent (as sulfuric acid). Substantial purification can be effected by slurrying the polymeric sulfonic acid derivatives in non-solvents therefor, such as the halocarbons. Removal of the free sulfuric acid is difficult, since it complexes strongly with the polymeric product. Diethyl ether is an exceptionally good complexing agent for sulfuric acid and effectively removes this contaminant when freshly isolated polymeric solids are slurried in the ether and filtered. Other effective additives for sulfuric acid removal are halocarbon solvent blends with diethyl ether and other oxygenated solvents, such as ethyl acetate and acetone. The sulfuric acid, if not removed, would result in contamination of the metal salts with, e.g. sodium sulfate, in the case where the sodium sulfonate polymer is produced.

The preferred process for purification of the sulfonated polymers, particularly highly water soluble types, is by dialysis in membrane tubes or hollow fiber dialyzing units having a molecular weight cut-off well below the molecular weight of the polymer. Dialysis removes all of the low molecular weight impurities and inorganic salts. High purity polymers are isolated as solids by freeze-drying or spray drying the dialyzed polymer solution.

The D.S. of the polymers, when sulfonated as described above, can be varied by adjusting the molar ratio of sulfonating agent to polymer. The D.S. of the formaldehyde polymers, either as their sulfonic acid or sulfonate salt derivatives, can be determined by any of several methods: (a) NMR analysis, (b) elemental analysis for sulfur to carbon ratio determination, (c) direct titration of the sulfonic acid derivative with standard sodium hydroxide to obtain the milliequivalents of sulfonic acid groups per gram of sample, a value approximately equivalent to the ion-exchange capacity of the sulfonated polymer, or (d) atomic absorption assay for the metal content of carefully purified samples of the sulfonated salts.

The alkali metal salts of the sulfonated polymers are conveniently prepared by neutralization of a water or alcohol solution of the polymeric sulfonic acid derivative with alkali metal hydroxide solutions to the potentionmetric endpoint. The salts are recovered by filtration, solvent stripping, or freeze drying, depending on the type of solvent used and whether the salt precipitates directly from the solvent media. Alternatively, sulfonate salts can be prepared by addition of at least stoichiometric quantities of an alkali metal oxide, carbonate, acetate, chloride, nitrate, or sulfate to the sulfonic acid derivative. The salts either precipitate directly and are collected, or they are isolated after solvent stripping. Purification of the sulfonate salt by dialysis is the preferred procedure for the more highly water soluble salts.

Multivalent metal salts, such as calcium, magnesium, zinc, and aluminum salts, of the sulfonated polymers are prepared by methods similar to those described above. In an alternate procedure, multivalent metal salts can be prepared by an ion-exchange reaction between the multivalent ion and either the free sulfonic acid or an alkali metal sulfonate derivative of the polymer. The neutralization and other salt forming reactions described above are essentially ion-exchange reactions. Ammonium salts of the sulfonic acid polymer can be prepared by direct addition of ammonia or a primary, secondary, or tertiary organic amine.

For testing the sulfonated formaldehyde polymers of this invention, the in vitro test procedure we have employed begins with growth of plaque in small jars containing sterilized trypticase media that has been supplemented with sucrose. Typically, ten jars are individually inoculated with 0.5 ml of unpooled freshly collected human plaque from 10 subjects. In a control series, a presterilized glass slide or an extracted human tooth is inserted into each jar. In the test series, the tooth or glass slide is pretreated with a 1% solution of the test compound (dissolved in water or other vehicle), allowed to dry in order to deposit a thin film of the compound on the surface, and the glass slide or tooth placed in the growth media. The jars are incubated under anaerobic conditions for two days at 37° C. The tooth or glass slide is removed, air dried, and stained with 0.15% FD&C #3 red dye solution to reveal the accumulated plaque deposits. The tooth or glass slide is scored for plaque density on a 0 to 5 scale. Plaque barrier activity is reported as the % of average plaque reduction, as compared to appropriate controls for ten subjects. As shown by the in vitro test results reported in Table 1, the sulfonated naphthalene formaldehyde polymers of this invention are highly effective in reducing the deposition of plaque. These polymers have a molecular weight in the range of from about 500 to about 5,000, preferably of the order of 2,000 to 3,000.

TABLE 1

Plaque Barrier Properties of Sulfonated Naphthalene Formaldehyde Polymers

| Polymer Source | Metal Salt | D.S. | % Plaque Reduction |
|---|---|---|---|
| TAMOL SN (commercial) | Na or Zn | 1.0 | 40 |
| Naphthalene/ formaldehyde condensate, | Na | 0.4 | 81 |
|  | Na | 0.8 | 56 |

TABLE 1-continued

Plaque Barrier Properties of Sulfonated Naphthalene Formaldehyde Polymers

| Polymer Source | Metal Salt | D.S. | % Plaque Reduction |
|---|---|---|---|
| sulfonated after condensation | Zn | 0.8 | 54 |
| Naphthalene-1-sulfonic acid/formaldehyde condensate | Na | 1.0 | 11 |
| Naphthalene-2-sulfonic acid/formaldehyde condensate | Na | 1.0 | 77 |

EXAMPLE 1

Naphthalene/Formaldehyde Polymer

A solution of 25.6 g (0.200 mole) naphthalene in 128 ml. glacial acetic acid, contaning 11.1 ml (0.200 mole) 96% sulfuric acid, was maintained at 116°–120° C. during addition, over 13 minutes, of 16 ml (0.200 mole) 37% formaldehyde solution. After heating and stirring at 111°–116° C. for two hours, the suspension of slightly gummy solids was cooled to room temperature and the reaction contents poured into 500 ml ice-water mixture. The solids were filtered, washed with water, and air dried. The polymer solids were dissolved in 70 ml. tetrahydrofuran and the solution added slowly to 700 ml. methanol with vigorous stirring to re-precipitate the purified polymer. The solids were collected, washed with methanol, and the precipitation procedure from tetrahydrofuran/methanol repeated. The yield of the naphthalene/formaldehyde polymer, showing a softening point of about 145° C., was 25.0 g. The weight average molecular weight, determined by light scattering in chloroform at room temperature, was $2300 \pm 100$.

EXAMPLE 2

Sulfonation of Naphthalene/Formaldehyde Polymer

A solution of 14.1 g of the naphthalene/formaldehyde polymer, prepared as in Example 1, in 70 ml. methylene chloride was stirred and maintained at 23° to 33° C. during the addition of a solution of 5.2 ml. (10.0 g, 0.125 mole) liquid sulfur trioxide in 80 ml. methylene chloride. After the addition period of 40 minutes, the resultant suspension of solids was stirred another one hour at the ambient temperature. The blue colored solids were filtered, washed with methylene chloride and ether, and dried to afford 21.2 g of the sulfonic acid derivative of the polymer as fine, blue solids.

Titration of an accurately weighed sample (2.8081 g) of the derivative in methanol with standard sodium hydroxide showed 3.87 milliequivalents/gram of sulfonic acid functionality, equivalent to a degree of sulfonation (D.S.) of 0.8. Removal of the solvent from the neutralized solution gave 2.7 g of the sodium sulfonate derivative as a dark orange, water soluble powder.

A solution of 10.0 g (38.7 meq. $SO_3H$) of the sulfonic acid derivative of the polymer in 60 ml. water was treated with a solution of 4.3 g (38.7 meq.) zinc acetate dihydrate in 20 ml. water, resulting in a pH increase from 1.7 to 3.9 and a color change from brown-green to brown-orange. The solution was stripped free of water under reduced pressure. The residue was taken up in 150 ml. water, centrifuged to clarify the solution, and the centrifugate stripped free of water under reduced pressure to afford 10.1 g of the zinc sulfonate salt, an orange powder. Dialysis of a 10% aqueous solution of the zinc sulfonate polymer in a Spectropor 6 membrane tube (molecular weight cutoff 2,000) gave an 88% recovery of purified zinc salt.

The plaque barrier oral compositions of this invention may comprise any conventional pharmaceutically acceptable oral hygiene formulation that contains (and is compatible with) an effective amount of a plaque barrier agent as defined herein. Such formulations include, for example, mouthwashes, rinses, irrigating solutions, abrasive and nonabrasive gel dentifrices, denture cleansers, coated dental floss and interdental stimulator coatings, chewing gums, lozenges, breath fresheners, foams and sprays.

The plaque barrier agents may be present in these formulations in effective concentrations generally in the range of from about 0.05 weight percent to as much as 30 weight percent or the limit of compatibility with the vehicle. However, no advantage will be derived from concentrations in excess of about 20 weight percent. A preferred concentration range for the plaque barrier agents in the formulations of the invention is from about 0.5 to about 10 weight percent. A more preferred range is from about 2 to about 8 percent by weight, about 5% being the presently most preferred concentration in a nonabrasive gel vehicle.

The pH of these plaque barrier preparations should be between pH 5.0 and 10.0, preferably between pH 5.0 and 8.0, more preferably between about pH 6.0 and 7.5. Lower pH than 5.0 is undesirable because of the possible enhancement of enamel demineralization.

Suitable conventional pharmaceutically acceptable vehicles that can be employed with the plaque barrier agents to prepare the barrier compositions of this invention may comprise water, ethanol; such humectants as polypropylene glycol, glycerol and sorbitol; such gelling agents as cellulose derivatives, for example, Methocel, carboxymethylcellulose (CMC TMF) and Klucel HF, polyoxypropylene/polyoxyethylene block copolymers, for example, Pluronic F-127, Pluronic F-108, Pluronic P-103, Pluronic P-104, Pluronic P-105, and Pluronic P-123, colloidial magnesium aluminosilicate complexes such as Veegum, and mucoprotein thickening agents such as Carbopol 934; gel stabilizers such as the silicon dioxides, for example, Cab-O-Sil M5, and polyvinylpyrrolidone; sweeteners such as sodium saccharin; preservatives such as citric acid, sodium benzoate, cetylpyridinium chloride, potassium sorbate, methyl and ethyl parabens; detergents such as sodium lauryl sulfate, sodium cocomonoglyceride sulfonate, sodium lauryl sarcosinate and polyoxyethylene isohexadecyl ether (Arlasolve 200) and approved colors and flavors.

The following specific examples will serve further to illustrate the plaque barrier compositions of this invention.

EXAMPLE A—Mouthwash Solution

| Barrier Agent | 0.5–2.0 % w/w |
|---|---|
| Glycerol (humectant) | 6.0 |
| Pluronic F-108 | 1.0 |
| Sodium saccharin (sweetener) | 0.3 |
| Deionized Water | q.s. |
| Flavors | 1.0 |
| | 100.0 |

EXAMPLE B—Mouthwash Solution

| Plaque Barrier Agent | 0.5–3.0 % w/w |
| --- | --- |
| Ethanol, USP | 15.0 |
| Pluronic F-108 (foaming agent) | 2.0 |
| Glycerol (humectant) | 10.0 |
| Sorbitol (humectant) | 10.0 |
| Sodium saccharin (sweetener) | 0.2 |
| Deionized Water | q.s. |
| Flavors | 0.2 |
| | 100.0 |

EXAMPLE C—Abrasive Dentifrice Gel

| Plaque Barrier Agent | 2.0–10.0 % w/w |
| --- | --- |
| Fumed Silica (abrasive) | 55.0 |
| Sodium Lauryl Sulfate (detergent) | 1.5 |
| Glycerol (humectant) | 10.0 |
| Carboxymethylcellulose (gelling agent) | 2.0 |
| Sodium saccharin (sweetener) | 0.2 |
| Sorbitol (humectant) | 10.0 |
| Flavors | 1.0 |
| Deionized Water | q.s. |
| Preservative | 0.05 |
| | 100.0 |

EXAMPLE D—Chewing Gum

| Plaque Barrier Agent | 1.0–11.0 % w/w |
| --- | --- |
| Gum Base | 21.3 |
| Sugar | 48.5–58.5 |
| Corn Syrup (Baume 45) | 18.2 |
| Flavors | 1.0 |
| | 100.0 |

EXAMPLE E—Nonabrasive Gel Dentifrice

| Plaque Barrier Agent | 0.05–30.0 % w/w |
| --- | --- |
| Sorbistat (preservative) | 0.15 |
| Deionized Water | q.s. |
| Silicon Dioxide (gel stabilizer) | 1.0 |
| Pluronic F-127 (gelling agent) | 20.0 |
| Sodium Saccharin | 0.2 |
| Flavors | 1.5 |
| | 100.0 |

EXAMPLE F

The following formulation illustrates a presently preferred nonabrasive gel composition containing a barrier agent in accordance with the present invention.

| Ingredients | % w/w |
| --- | --- |
| Distilled Water | q.s. |
| Sodium Saccharin (sweetener) | 0.20 |
| Sodium Benzoate (preservative) | 0.30 |
| FD & C Blue #1 (0.1% aq. soln.) | 0.27 |
| D & C Yellow #10 (0.5% aq. soln.) | 0.50 |
| Gelling agent | 18.00 |
| Glycerol (Humectant) | 20.00 |
| Cab-O-Sil M5 (Silicon Dioxide) | 1.00 |
| Plaque Barrier Agent | 5.00 (dry basis) |
| Flavor | 0.80 |
| | 100.0 |

While the details of preparing all of the above formulations are well within the skill of the art, a suggested procedure for preparing the gel formulation of this example will be described for completeness.

In a first container the water, sodium saccharin, sodium benzoate and dyes are mixed. Then the container is put into an ice bath. When the temperature reaches 6° C., the gelling agent is added and the contents mixed slowly until the gelling agent is dissolved. Then the solution is heated to 70° C.

Into a second container is added the glycerin. Then the Cab-O-Sil M5 is sprinkled in with mixing. Then the plaque barrier agent is added and mixing continued to a smooth paste. The paste is then heated in a water bath with mixing to a temperature of 70° C.

The contents of the first container are added to the second container and blended together until the batch is homogenous while maintaining a 70° C. temperature. Then the flavoring is added, all mixing is stopped, and the formulation allowed to settle for approximately one hour. If necessary to remove air bubbles, overnight refrigeration may be employed.

While any pharmaceutically acceptable gelling agent that is compatible with the plaque barrier agent may be employed, a presently preferred gelling agent is Pluronic F-127.

These compositions are preferably employed from one to three times daily in a routine oral hygiene program to prevent the attachment of plaque to the teeth.

Variations can, of course, be made without departing from the spirit or scope of the invention.

I claim:

1. An oral hygiene composition comprising an effective amount for preventing deposition of dental plaque on teeth of a sulfonated condensation polymer of formaldehyde with naphthalene, said polymer having repeating units of structure:

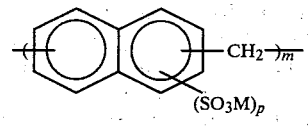

wherein M is selected from the group consisting of lithium, sodium, potassium, calcium, magnesium, zinc, aluminum, hydrogen, ammonium, and substituted ammonium ions derived from pharmaceutically acceptable organic amines, and p has an average value in the range of from about 0.4 to about 1.4, said polymer having a molecular weight in the range of from about 500 to about 5,000, in a pharmaceutically acceptable oral hygiene vehicle compatible with said polymer.

2. The composition of claim 1 wherein M is a metal selected from the group consisting of potassium, lithium, sodium, calcium, magnesium, zinc and aluminum.

3. The composition of claim 1 wherein p is about 1.

4. The composition of claim 3 wherein said polymer is a condensation polymer of formaldehyde with 2-naphthalene sulfonic acid.

5. The composition of claim 4 wherein said polymer has a molecular weight of from about 2,000 to about 3,000.

6. A method of preventing deposition of dental plaque on teeth comprising periodically applying to the teeth a composition of claim 1.

7. The method of claim 6 wherein said composition is applied from about 1 to about 3 times per day.

8. The composition of claim 1 in the form of an oral hygiene formulation selected from the group consisting of mouthwashes, mouthrinses, irrigating solutions, abrasive gel dentifrices, non-abrasive gel dentifrices, denture cleansers, coated dental floss, coated interdental stimulators, chewing gums, lozenges, breath fresheners, foams and sprays.

* * * * *